(12) United States Patent
Sudo et al.

(10) Patent No.: US 7,825,061 B2
(45) Date of Patent: Nov. 2, 2010

(54) CATALYST FOR PRODUCING METHACRYLIC ACID AND PREPARATION METHOD THEREOF

(75) Inventors: Atsushi Sudo, Annaka (JP); Yoshimasa Seo, Takasaki (JP); Hideki Sugi, Sawa-gun (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 610 days.

(21) Appl. No.: 10/545,699

(22) PCT Filed: Feb. 20, 2004

(86) PCT No.: PCT/JP2004/001999

§ 371 (c)(1),
(2), (4) Date: Oct. 3, 2005

(87) PCT Pub. No.: WO2004/073857

PCT Pub. Date: Sep. 2, 2004

(65) Prior Publication Data

US 2006/0154811 A1 Jul. 13, 2006

(30) Foreign Application Priority Data

Feb. 20, 2003 (JP) .............................. 2003-042259

(51) Int. Cl.
- B01J 27/00 (2006.01)
- B01J 27/198 (2006.01)
- B01J 27/188 (2006.01)
- B01J 27/19 (2006.01)
- B01J 27/192 (2006.01)
- B01J 27/185 (2006.01)

(52) U.S. Cl. ....................... 502/208; 502/209; 502/210; 502/211; 502/212; 502/213

(58) Field of Classification Search .......... 502/208–213
See application file for complete search history.

(56) References Cited

U.S. PATENT DOCUMENTS

| | | | | |
|---|---|---|---|---|
| 4,180,678 A | * | 12/1979 | Wada et al. | 562/534 |
| 4,558,028 A | * | 12/1985 | Tsuneki et al. | 502/211 |
| 4,652,673 A | * | 3/1987 | Matsumoto et al. | 562/535 |
| 4,925,980 A | * | 5/1990 | Matsumoto et al. | 562/534 |
| 5,104,844 A | | 4/1992 | Yamamoto et al. | 502/200 |
| 6,043,184 A | * | 3/2000 | Karmakar et al. | 502/208 |
| 6,458,740 B2 | * | 10/2002 | Kasuga et al. | 502/211 |
| 6,812,188 B2 | * | 11/2004 | Seo et al. | 502/208 |
| 2001/0029233 A1 | | 10/2001 | Kasuga et al. | 502/211 |
| 2007/0010394 A1 | * | 1/2007 | Atsushi et al. | 502/200 |

FOREIGN PATENT DOCUMENTS

| | | |
|---|---|---|
| EP | 0 006 248 | 1/1980 |
| EP | 0 442 517 | 8/1991 |
| EP | 0 454 376 | 10/1991 |
| EP | 0454376 | 10/1991 |
| EP | 1 132 131 | 9/2001 |
| EP | 1 325 780 | 7/2003 |
| JP | 3-238052 | 10/1991 |
| JP | 11-226411 | * 8/1999 |
| JP | 11-226412 | 8/1999 |
| JP | 11226412 | 8/1999 |
| JP | 2000-296336 | 10/2000 |
| JP | 2001-246260 | 9/2001 |
| JP | 2002-233760 | 8/2002 |
| KR | 1993-5306 | 6/1993 |
| KR | 10-2005-0098919 | * 10/2005 |
| WO | 02/24328 | 3/2002 |
| WO | 0224328 | 3/2002 |

OTHER PUBLICATIONS

Supplemental European Search Report dated Jan. 31, 2007.
International Search Report Jun. 1, 2004.
Chinese communication dated Jun. 8, 2007.
European communication dated Jul. 2, 2009.
Korean communication dated Feb. 27, 2010, with English translation in co-pending application (10-2005-7014828).
Taiwanese communication dated Jun. 14, 2010 in co-pending foreign application (TW093104115).

* cited by examiner

*Primary Examiner*—Patricia L Hailey
(74) *Attorney, Agent, or Firm*—Nields, Lemack & Frame, LLC

(57) ABSTRACT

The object of the present invention is to provide a catalyst for producing methacrylic acid in high yield and highly selectively by subjecting methacrolein, isobutylaldehyde or isobutyric acid to gas phase catalytic oxidation, and the preparation method thereof. The catalyst contains Mo, V, P, Cu, Cs and $NH_4$ as the essential, active components, and the feature is to use for preparing the catalyst a cesium weak acid salt or cesium hydroxide as the Cs raw material and ammonium acetate as the $NH_4$ raw material. A coated catalyst of the present invention is obtainable by supporting the active component on an inert carrier of alumina or the like.

10 Claims, No Drawings

CATALYST FOR PRODUCING METHACRYLIC ACID AND PREPARATION METHOD THEREOF

TECHNICAL FIELD

The present invention relates to a catalyst for producing methacrylic acid by subjecting methacrolein, isobutylaldehyde or isobutyric acid to gas phase catalytic oxidation, having a long life, a high activity as well as high selectivity, and the preparation method thereof.

BACKGROUND ART

A large number of catalysts for producing methacrylic acid by subjecting methacrolein, isobutylaldehyde or isobutyric acid to gas phase catalytic oxidation, have been proposed. Most of the catalysts thereof are mainly composed of molybdenum and phosphorus, and have structures of heteropolyacids and/or salts thereof. The catalysts used in the reaction, however, have low reaction activities, low selectivity for the desired substance, and short lives, as compared to molybdenum-vanadium based catalysts used in reactions for producing acrylic acid by subjecting acrolein to gas phase catalytic oxidation, which are known as reactions similar to the reaction for producing methacrylic acid. Accordingly, the improvement of catalytic performance of the catalysts is required although some of the catalysts are industrially utilized.

The present inventors first tried the improvement of low activities, low selectivity and short lives of conventional gas phase catalytic oxidation catalysts for methacrolein, and found out that gas phase catalytic oxidation catalysts for methacrolein prepared by the addition of a variety of elements to Mo, V and P, have heteropolyacid (salt) structures and have high activities, high selectivity and are particularly stable for the time lapse. The inventors propose the catalysts described in Japanese Patent Publication No. 58-11416, Japanese Patent Publication No. 59-24140, Japanese Patent Publication No. 62-14535 and Japanese Patent Publication No. 62-30177.

Recently, because of high concentrations of raw material gases and of environments under which oxidation reactions are conducted at elevated temperature, catalysts that exhibit further high activities, high selectivity and long lives, are needed. Various preparation methods are proposed to provide catalysts that satisfy these demands. For example, Japanese Patent Laid-Open No. 5-31368 and Japanese Patent Laid-Open No. 8-196908 propose methods for preparing molding catalysts that involve using $NH_4$ in addition to the components of Mo, V and P, and utilizing aqueous ammonia as the ammonium source. In addition, Japanese Patent Laid-Open No. 11-226411 describes a method for preparing a molding catalyst that comprises using refined starch when an active component of the catalyst is granulated, and improving the pore volume of the catalyst by burning the starch in the calcining step.

Furthermore, when a catalyst is loaded in a fixed-bed reactor as an industrial catalyst, the catalyst is required to be molded to a constant size in order to reduce the pressure drop of the reaction gas prior to and subsequent to the catalyst layer. For this purpose, known methods involve normally molding a catalyst powder to a cylindrical material, a pellet, a ring-shaped material, a sphere-shaped material, or the like, and impregnating or coating an inert carrier with an active catalyst material also.

Advantages of a coated catalyst having the inert carrier as the core include [1] being capable of improving the effective utilization factor of active components of the catalyst, [2] being expected to improve the selectivity due to the homogeneous distribution of the residence time of reaction materials within the catalyst, and [3] facilitating the removal of the reaction heat on account of the improvement of the catalyst thermal conductivity or the dilution effect of the inert carrier. As a result, there are many examples applied to selective oxidation of a large heat release.

On the other hand, technical disadvantages in preparing a coated catalyst include [1] the peeling of the coating layer and the difficulty of obtaining a mechanically strong catalyst because the catalyst is subject to cracking, [2] the difficulty of coating a carrier with a large amount of active catalytic material, and [3] the difficulty of obtaining a highly active catalyst due to inclusion of inert materials.

Methods for overcoming the disadvantages are related to the properties of active catalyst substances and the present situation is to study catalysts individually because of no general techniques.

DISCLOSURE OF THE INVENTION

The object of the present invention is to provide a catalyst or a coated catalyst for producing methacrylic acid in high yield and highly selectively by subjecting methacrolein, isobutylaldehyde or isobutyric acid to gas phase catalytic oxidation, and the preparation methods thereof.

The present inventors have tried to improve the low activities, low selectivity and short lives of conventional gas phase catalytic oxidation catalysts for methacrolein as a method for solving the above-mentioned problems, and found out that when preparing a catalyst containing the essential components of Mo, V, P, Cu, Cs and $NH_4$, i.e. when preparing a heteropoly acid (salt) containing the essential components, an industrial catalyst offering a high activity, high selectivity and being particularly stable for the time lapse can be obtained when a cesium weak acid salt or cesium hydroxide is added as the Cs raw material and ammonium acetate or ammonium hydroxide is added as the $NH_4$ raw material, with the completion of the present invention.

That is to say, the present invention relates to:

(1) A catalyst for producing methacrylic acid by subjecting methacrolein, isobutylaldehyde or isobutyric acid to gas phase catalytic oxidation, having as an active component of the catalyst a heteropoly acid salt comprising a heteropoly acid in which Mo, V, P, Cu, Cs and $NH_4$ are contained as the essential, active components, characterized in that the catalyst is obtainable by using a cesium weak acid salt or cesium hydroxide as the Cs raw material and ammonium acetate as the $NH_4$ raw material, of the active component of the catalyst.

(2) The catalyst described in (1) above, wherein the Cs raw material is cesium acetate or cesium hydroxide.

(3) The catalyst described in (1) or (2) above, wherein the catalyst does not contain arsenic as an active component.

(4) The catalyst described in any one of (1) to (3) above, wherein copper acetate or cupric oxide is used as the copper raw material of the catalyst.

(5) The catalyst described in any one of (1) to (4), wherein the composition of the active component of the catalyst is represented by the formula (1):

$$Mo_{10}V_aP_bCu_cCs_d(NH_4)_eX_fO_g \qquad (1)$$

wherein Mo is molybdenum, V is vanadium, P is phosphorus, Cu is copper, Cs is cesium, $(NH_4)$ is ammonium group, X is one or more elements selected from the group consisting of Sb, As, Ag, Mg, Zn, Al, B, Ge, Sn, Pb, Ti, Zr, Cr, Re, Bi, W, Fe, Co, Ni, Ce, Th, K and Rb, a to g represent the atomic ratio of each element, a is a positive number of $0.1 \leqq a \leqq 6.0$, b is a positive number of $0.5 \leqq b \leqq 6.0$, c is a positive number of $0 < c \leqq 3.0$, d is a positive number of $0.01 \leqq d \leqq 3.0$, e is a positive number of $0.1 \leqq e \leqq 3.0$, f is a positive number of $0 \leqq f \leqq 3.0$, and g is a value determined by the oxidation number of an acid of each element.

(6) The catalyst described in (5) above, wherein a is a positive number of $0.5 \leqq a \leqq 1.2$, b is a positive number of $0.9 \leqq b \leqq 1.5$, c is a positive number of $0.2 \leqq c \leqq 0.8$, d is a positive number of $0.2 \leqq d \leqq 0.8$, e is a positive number of $1.0 \leqq e \leqq 2.2$, and f is a positive number of $0 \leqq f \leqq 0.8$.

(7) The catalyst described in (5) or (6) above, wherein the catalyst contains Sb as an essential element.

(8) A method for preparing a catalyst for producing methacrylic acid by subjecting methacrolein, isobutylaldehyde or isobutyric acid to gas phase catalytic oxidation, the method comprising:

step (A) of blending compounds A-1 to A-3 and, as needed, compound A-4 with water to prepare an aqueous solution or dispersion of the compounds (hereinafter, called a slurry, including both), wherein the compound A-1 is a compound containing Mo, a compound containing V, a compound containing P, and a compound containing Cu, the compound A-2 is a cesium weak acid salt or cesium hydroxide, the compound A-3 is ammonium acetate, and the compound A-4 is one or more compounds selected from the group consisting of compounds containing one of Sb, As, Ag, Mg, Zn, Al, B, Ge, Sn, Pb, Ti, Zr, Cr, Re, Bi, W, Fe, Co, Ni, Ce, Th, K and Rb; and step (B) of drying the slurry yielded in step (A) to obtain a dried slurry.

(9) The method for preparing the catalyst described in (8) above, wherein the compound A-4 is used as an essential component.

(10) A method for preparing a coated catalyst for producing methacrylic acid by subjecting methacrolein, isobutylaldehyde or isobutyric acid to gas phase catalytic oxidation, the method comprising:

step (a) of blending compounds a-1 to a-3 and, as needed, compound a-4 with water to prepare an aqueous solution or dispersion of the compounds (hereinafter, called a slurry, including both), wherein the compound a-1 is a compound containing Mo, a compound containing V, a compound containing P, and a compound containing Cu, the compound a-2 is a cesium weak acid salt or cesium hydroxide, the compound a-3 is ammonium acetate or ammonium hydroxide, and the compound a-4 is one or more compounds selected from the group consisting of compounds containing one of Sb, As, Ag, Mg, Zn, Al, B, Ge, Sn, Pb, Ti, Zr, Cr, Re, Bi, W, Fe, Co, Ni, Ce, Th, K and Rb;

step (b) of drying the slurry yielded in step (a) to obtain a dried slurry;

step (c) of coating a carrier with the dried slurry obtained in step (b) using a binder to obtain a coated molded product; and step (d) of calcining the coated molded product obtained in step (c).

(11) A method for preparing a coated catalyst for producing methacrylic acid by subjecting methacrolein, isobutylaldehyde or isobutyric acid to gas phase catalytic oxidation, the method comprising:

step (a) of blending compounds a-1 to a-3 and, as needed, compound a-4 with water to prepare a slurry of the compounds, wherein the compound a-1 is a compound containing Mo, a compound containing V, a compound containing P, and a compound containing Cu, the compound a-2 is a cesium weak acid salt or cesium hydroxide, the compound a-3 is ammonium acetate or ammonium hydroxide, and the compound a-4 is one or more compounds selected from the group consisting of compounds containing one of Sb, As, Ag, Mg, Zn, Al, B, Ge, Sn, Pb, Ti, Zr, Cr, Re, Bi, W, Fe, Co, Ni, Ce, Th, K and Rb;

step (b) of drying the slurry yielded in step (a) to obtain a dried slurry;

step (b') of blending the dried slurry obtained in step (b) with a solid compound containing copper to obtain powders;

step (c) of coating a carrier with the powders obtained in step (b') using a binder to obtain a coated molded product; and step (d) of calcining the coated molded product obtained in step (c).

(12) The method for preparing the coated catalyst described in (10) or (11) above, wherein the compound a-4 is used as an essential component.

(13) The method for preparing the coated catalyst described in any one of (10) to (12) above, wherein at least one species selected from the group consisting of water and organic compounds having a boiling point of 150° C. or lower at one atmospheric pressure is used as a binder.

(14) The method for preparing the coated catalyst described in (13) above, wherein the binder is ethanol.

(15) The method for preparing the coated catalyst described in (13) above, wherein the binder has a weight ratio of ethanol to water being from 10:0 to 5:5.

(16) The method for preparing the coated catalyst described in any one of (10) to (15) above, wherein the coated molded product is calcined in the presence of a reducing agent in step (d).

(17) The method for preparing the coated catalyst described in (16) above, wherein the reducing agent is ethanol.

(18) A coated catalyst for producing methacrylic acid by subjecting methacrolein, isobutylaldehyde or isobutyric acid to gas phase catalytic oxidation, obtainable from the method described in any one of (10) to (17) above.

ADVANTAGES OF THE INVENTION

The catalysts of the present invention are capable of producing methacrylic acid from methacrolein, isobutylaldehyde or isobutyric acid in high yield and highly selectivity, and further of being used for reactions under high loaded conditions, and thus have extremely large industrial values.

BEST MODE FOR CARRYING OUT THE INVENTION

First, a catalyst prepared by using a cerium weak acid salt or cerium hydroxide and ammonium acetate, a first embodiment of the present invention, will be described.

A preferable method for obtaining a catalyst of the present invention involves dissolving and/or dispersing in water a plurality of compounds containing each of or a plurality of Mo, V, P, Cu, Cs and $NH_4$ and, as needed, other elements (hereinafter, in some cases, the compounds including the active components being also called "active components-containing compound"), using a cesium weak acid salt or cesium hydroxide as a cesium compound and ammonium acetate as an ammonium compound when preparing a slurry (step A), and drying the resultant slurry (step B).

In the present invention, an active components-containing compound used for preparing a slurry other than that of a cesium weak acid salt, cerium hydroxide and ammonium acetate is preferably a compound that forms a heteropoly acid or a salt thereof by drying (step B) or calcining. The compound includes chlorides, sulfates, nitrates, oxides and acetates, of the active component elements. Preferable examples of the compound include nitrates such as potassium nitrate and cobalt nitrate, oxides such as molybdenum oxide, vanadium pentaoxide, antimony trioxide, cerium oxide, zinc oxide and germanium oxide, and acids (and the salts thereof) such as orthophosphoric acid, phosphoric acid, arsenic acid, ammonium phosphate and 12-tungstophosphoric acid. In addition, use of copper acetates (copper(I) acetate, copper(II) acetate, basic copper acetates, cupric oxide and so forth, preferably copper(II) acetate) sometimes leads to a preferable effect. These may be used solely or in a mixture of two or more species.

Cesium weak acid salts are not particularly limited if the salts are salts between cesium and generally known weak acids. The salts include, for example, cesium hydrogencarbonate, cesium carbonate and cesium acetate, and cesium acetate is preferable. Additionally, of these, although commercially available cesium acetate can be used directly, for example, an aqueous cesium acetate solution obtained by adding to an aqueous solution of a water-soluble salt of cesium such as cesium hydroxide or cesium carbonate one or more equivalents of acetic acid, may also be used.

In the present invention, an active component other than Mo, V, P, Cu, Cs and $NH_4$ are not particularly limited if the component is a compound from the elements known as the component elements of the catalyst for producing methacrylic acid. The elements contained in the compound include one or more species selected from the group consisting of Sb, As, Ag, Mg, Zn, Al, B, Ge, Sn, Pb, Ti, Zr, Cr, Re, Bi, W, Fe, Co, Ni, Ce, Th, K and Rb. Of these, the elements excluding As are preferable.

For the ratio of each active component of a catalyst in the present invention, based on a molybdenum's atomic ratio of 10, the ratio of vanadium is normally from 0.1 to 6.0, both inclusive, preferably from 0.3 to 2.0, both inclusive, particularly preferably from 0.5 to 1.2, both inclusive, the ratio of phosphorus is normally from 0.5 to 6.0, both inclusive, preferably from 0.9 to 1.5, both inclusive, the ratio of copper is normally from 0 exclusive to 3.0 inclusive, preferably from 0.01 to 1.0, both inclusive, particularly preferably 0.2 to 0.8, both inclusive, the ratio of cesium is normally from 0.01 to 3.0, both inclusive, preferably from 0.1 to 1.5, both inclusive, particularly preferably from 0.2 to 1.0, both inclusive, the ratio of ammonium is normally from 0.1 to 3.0, both inclusive, preferably from 0.5 to 3.0, both inclusive, particularly preferably from 1.0 to 2.2, both inclusive. The kinds and the use ratios of other active components necessary for use are determined, as appropriate, in such a way that a catalyst having the best suitable performance is obtainable, in accordance with the use conditions, etc. of the catalyst. A preferable catalyst used under normal conditions is one having an active component composition represented by the formula (1):

$$Mo_{10}V_aP_bCu_cCs_d(NH_4)_eX_fO_g \qquad (1)$$

wherein Mo is molybdenum, V is vanadium, P is phosphorus, Cu is copper, Cs is cesium, ($NH_4$) is ammonium group, X is one or more elements selected from the group consisting of Sb, As, Ag, Mg, Zn, Al, B, Ge, Sn, Pb, Ti, Zr, Cr, Re, Bi, W, Fe, Co, Ni, Ce, Th, K and Rb, a to g represent the atomic ratio of each element, a is a positive number of $0.1 \leq a \leq 6.0$, b is a positive number of $0.5 \leq b \leq 6.0$, c is a positive number of $0 < c \leq 3.0$, d is a positive number of $0.01 \leq d \leq 3.0$, e is a positive number of $0.1 \leq e \leq 3.0$, f is a positive number of $0 \leq f \leq 3.0$, and g is a value determined by the oxidation number of each element. In addition, the active component composition thereof means the component in the dried slurry below and does not necessarily reflect the composition of the powder via step (d). Namely, because of a calcining temperature and a calcining time in the calcining step (step (d)), $NH_4$ component may evaporate and be substituted with a hydrogen or metal atom. According to the findings of the present inventors, $NH_4$ component in the dried slurry sometimes evaporates by passing through the calcining step. The evaporation level of $NH_4$ depends on a calcining temperature, calcining time and calcining atmosphere, i.e. under the air or nitrogen, and reaches up to about 90 mole %.

In the formula (1) above, element X is preferably Sb. Sb is used, as necessary, in the range of 0 to 2.2, both inclusive, preferably from 0.01 to 0.8, both inclusive, in the formula (1) above.

The catalyst can be obtained in the following procedure.

First, an aqueous solution or dispersion of the active components-containing compound (hereinafter, called a slurry, including both) is prepared. The slurry can be obtained by uniformly blending a plurality of compounds containing each active component with a solvent, preferably water. The slurry preferably contains all the compounds containing necessary active components in the needed amount of catalyst. The order of addition of compounds containing active components when the slurry is prepared is not specifically limited, but it is preferable that, first, compounds containing Mo, V and P are made a slurry and then to the slurry are added a compound containing a cesium weak acid salt or cesium hydroxide, ammonium acetate and copper.

The temperature when the slurry is prepared is not particularly limited unless causing troubles, and the temperature when a cesium weak acid salt or cesium hydroxide, ammonium acetate and a copper-containing compound is normally from 0 to 35° C., preferably from 10 to 30° C., which sometimes results in making the resultant catalyst highly active. The tendency is remarkable when copper acetate is used as a copper-containing compound, and so the adoption of the above-mentioned, preferable method of addition for preparing a slurry is rather efficient.

In the present invention, a slurry is preferably an aqueous solution. The use ratio of a compound containing each active component in a slurry is not particularly limited if the atomic ratio of each active component is within the above-described range. The amount of use of water is not particularly limited if compounds to be used can be dissolved completely or homogeneously blended, and is determined taking into account the drying method, drying conditions, etc. described below. That is, the amount of water is about 200 to 2000 parts by weight, based on the total amount, 100 parts by weight, of compounds for preparing a slurry. Although a large amount of water may be usable, but the amount much more than the normal amount leads to many demerits, including a high energy cost in the drying step as well as sometimes causing incomplete drying, and so the suitable amount is preferable.

Next, the slurry obtained above is dried to be made a dried slurry. A method for drying is not particularly limited if the slurry can completely be dried, and, methods include, for example, drum drying, freeze drying, spray drying, and evaporation drying. Of these, in the present invention, the spray drying, which allows a slurry state to dry to a powder or a granule in a short time, and the evaporation drying, which directly dries the slurry simply and easily, are preferable, and the evaporation drying is particularly preferable.

The temperature of the spray drying varies depending on the concentration and the transport rate of a slurry, and the temperature of the exit of a drier is generally from 70 to 150° C. In addition, the average particle diameter of the resultant dried slurry is preferably dried to be from about 30 to 500 μm. The evaporation drying may be carried out according to the standard method, and in this case a dried slurry is obtained as clusters or as large particles, and thus is ground, as appropriate, for use such that the size is preferably 300 μm or less. In the present invention, a dried slurry includes such a ground slurry.

The dried slurry obtained in this way can be utilized for gas phase catalytic oxidation as a catalyst of the present invention and, as described previously, the slurry is preferably formed into a cylindrical material, a pellet, a ring-shaped material or sphere-shaped material for the purpose of reducing the pressure loss of reaction gas. For these, due to being expected to improve selectivity and remove reaction heat, it is particularly preferable that an inert carrier is coated with the dried slurry to obtain a coated catalyst. Furthermore, in step (A) a slurry is prepared without using a copper-containing compound, and the slurry is supplied to the drying step, and then the resultant dried material is blended with a powder of the copper-containing compound to be able to obtain a catalyst of the present invention as well.

In the following, a method for preparing a coated catalyst, a second embodiment of the present invention, will be set forth.

A coated catalyst of the present invention can be prepared as for the preparation of the dried slurry described above except that ammonium hydroxide can further be selected as an ammonium source in step (A). In other words, raw compounds are dissolved and/or dispersed in water to prepare a slurry (step (a)) and this is dried to obtain a dried slurry (step (b)). In step (a) the order of addition of each raw compound is not particularly restricted, but as in step (A) it is rather preferable that compounds containing Mo, V and P are first made a slurry, and subsequently compounds to be a cesium source, an ammonium source and a copper source are added to the slurry. For step (a) as well, the temperature when a cesium source, an ammonium source and a copper source are added is normally from 0 to 35° C., preferably from 10 to 30° C.

Additionally, in step (a) a slurry is prepared without using a copper-containing compound, and the slurry is supplied to the drying step, and then the resultant dried material is blended with a powder of the copper-containing compound to obtain a mixture (step (b')), from which a coated catalyst of the present invention can be obtained as well.

The resultant dried slurry (or the mixture described above, hereinafter, the dried slurry includes the above-mentioned mixture) is supplied to the coating step described below (step c)).

For the coating step (step (c)) the rolling granulating process described below is preferable. This process involves vigorously agitating, for example, using a device having an even or uneven disc at the bottom of a fixed vessel, a carrier in the vessel by rotating the disc at a high speed and thus repeating the rotation and revolution of the carrier and adding to this an mixture of a binder and a dried slurry and, as needed, other additives, such as a molding aid and a strength-improving material, to coat the carrier with the mixture. Methods of adding a binder can adopt any method of [1] adding in advance the above-mentioned mixture to the binder, [2] adding the binder simultaneously with adding the mixture to the fixed vessel, [3] adding the binder after adding the mixture to the fixed vessel, [4] adding the binder prior to adding the mixture to the fixed vessel, [5] separating the mixture and the binder and adding the total amount in a combination of, as appropriate, [2] to [4]. Of these, for [5], for example, the speed of addition is preferably adjusted with an auto-feeder or the like in such a manner that a specified amount of mixture is supported on the carrier without adherence of the mixture on the fixed vessel wall and coagulation of the mixture particles with each other.

A binder is not particularly limited if it is at least one species selected from the group consisting of water and organic compounds having a boiling point of 150° C. or lower at one atmospheric pressure, and a binder having a boiling point of 100° C. or lower is preferable considering drying after coating, etc. Examples of binders except water include alcohols such as methanol, ethanol, propanols and butanols, preferably alcohols having a carbon number of 1 to 4, ethers such as ethyl ether, butyl ether and dioxane, esters such as ethyl acetate and butyl acetate, ketones such as acetone and methyl ethyl ketone, and aqueous solutions thereof, and ethanol is particularly preferable. When ethanol is used as a binder, the ratio by weight of ethanol to water is from 10:0 to 5:5, preferably from 10:0 to 7:3, particularly preferably about 10 to 30% by weight in ethanol concentration. The amount of use of a binder is normally from 2 to 60 parts by weight, preferably from 5 to 25 parts by weight, based on 100 parts by weight of a dried slurry.

Examples of carriers capable of being used in the present invention include silicon carbide, alumina, silica alumina, mullite, and alundum, which are sphere carriers and have a diameter of from 1 to 15 mm, preferably from 2.5 to 10 mm, and particularly preferably from 2.5 to 4.5 mm. The pore ratio of carrier for use is normally from 10 to 70%. The pore ratio of carrier is defined as $(W_3-W_1)/(W_3-W_2)*100$, wherein $W_1$ is a dry carrier weight, $W_2$ is a carrier weight in water, and $W_3$ is a carrier weight at saturation with water absorbed. The ratio of a coating dried slurry to (the dried slurry+a carrier) is normally from 10 to 75% by weight, preferably from 15 to 60% by weight.

When the ratio of a coating dried slurry is large, the reaction activity of the coated catalyst tends to become large, but the mechanical strength tends to be small (the degree of friction being large). Inversely, when the ratio of a coating dried slurry is small, the mechanical strength is prone to be large (the degree of friction being small), but the reaction activity is prone to be small.

In the present invention, when a carrier is coated with a dried slurry, a molding aid such as silica gel, diatomite or an alumina powder may further be used, as needed. The amount of molding aid for use is normally from 5 to 60 parts by weight based on 100 parts by weight of the dried slurry.

In addition, use of additional, as needed, inorganic fibers such as ceramic fibers and whisker as a strength-improving material is useful to improve the mechanical strength of the catalyst. However, fibers, which react with catalyst components, such as potassium titanate whisker and basic magnesium carbonate whisker are unsuitable. The amount of use of the fibers is normally from 1 to 30 parts by weight based on 100 parts by weight of the dried slurry.

Additives such as the molding aid and the strength-improving material above are introduced into a granulating machine normally in the coating step along with a carrier, a dried slurry, a binder, etc. to be used to coat the carrier.

In this way, a carrier is coated with a dried slurry, and the coated product obtained normally has a diameter of about 3 to 15 mm, preferably about 3.2 to 5 mm.

A coated catalyst obtained in this way can directly be supplied to gas phase catalytic oxidation as a catalyst. It is preferable that the catalyst is calcined (step (d)), sometimes causing the improvement of the catalyst activity. In this case, the calcining temperature is normally from 100 to 420° C., preferably from 250 to 400° C. and the calcining time is from 1 to 20 hours.

In addition, calcining is normally carried out under an aerial atmosphere, may be conducted under an inert gas atmosphere, or after calcining under an inert gas atmosphere, additional calcining, as required, may be performed under an aerial atmosphere. Furthermore, it is preferable that calcining is carried out under an inert gas atmosphere, preferably in the presence of a reducing agent, which sometimes leads to obtaining a catalyst with a higher activity. A reducing agent is not particularly limited if the agent preferably becomes gaseous at the calcining temperature. Examples of reducing agents include CO, alcohols having a carbon number of 2 to 5, aldehydes, ketones and organic acids, and ethanol is particularly preferable.

A catalyst of the present invention obtained as described above is used when methacrylic acid is produced by subjecting methacrolein, isobutylaldehyde or isobutyric acid to gas phase catalytic oxidation. Additionally, catalysts of the present invention include, unless otherwise stated, both a dried slurry obtained via steps (A) and (B) and a coated catalyst obtained via steps (a) to (c) (and preferably further via step (d)).

Hereinafter, a gas phase catalytic reaction of methacrolein, which is the most preferable raw material in the case of using a catalyst of the present invention, will be set forth.

Molecular oxygen or a gas containing molecular oxygen is used for gas phase catalytic oxidation. The molar ratio, for use, of molecular oxygen to methacrolein is preferably from 0.5 to 20, particularly preferably from 1 to 10. Water is preferably introduced into raw material gases in a molar ratio of water to methacrolein being from 1 to 20 in order to allow the reaction to smoothly proceed.

The raw material gases may contain oxygen and, as needed, inert gases, such as nitrogen, carbon dioxide gas and saturated hydrocarbon, in addition to water (normally contained as water vapor).

Further, for methacrolein, gas obtained by oxidizing isobutylene, tertiary butanol and methyl tertiary butylether may directly be supplied.

The reaction temperature of the gas phase catalytic oxidation is normally from 200 to 400° C., preferably from 260 to 360° C. With the amount of supply of raw material gases, the space velocity (SV) is normally from 100 to 6000 hr$^{-1}$, preferably from 400 to 3000 hr$^{-1}$.

Use of a catalyst of the present invention does not change the reaction merit even though the SV is increased, and allows the reaction to proceed at a high space velocity.

In addition, the catalytic oxidation is possible at an increased pressure or at a reduced pressure as well, and a pressure near an atmospheric pressure is normally suitable.

EXAMPLES

Hereinafter, the present invention will be described further specifically using Examples and Comparative Examples.

Additionally, in Examples and Comparative Examples below, the degree of conversion, selectivity and yield are defined as follows:

Conversion degree=(molar number of reacted methacrolein/molar number of supplied methacrolein)×100

Selectivity=(molar number of produced methacrolein/molar number of reacted methacrolein)×100

Yield=(molar number of produced methacrolein/molar number of supplied methacrolein)×100

Furthermore, the catalytic, active components composition in the Examples all are ratios calculated from loaded raw materials. In addition, Formulae are indicated without oxygen.

Example 1

1) Preparation of Catalyst

To 1200 mL of purified water were added 200 g of molybdenum trioxide, 8.84 g of vanadium pentaoxide and 17.61 g of 85 wt % orthophosphoric acid, and the solution was heated at reflux at 90 to 100° C. for five hours to yield a reddish-brown, transparent solution.

Subsequently, to the solution was added 6.07 g of antimony trioxide and the resultant solution was further heated at reflux at 90 to 100° C. for two hours to obtain an antimony trioxide-dissolved, highly dark blue solution.

Then, the resulting solution was cooled to from 15 to 20° C. To the solution were gradually added a solution of 13.33 g of cesium acetate dissolved in 150 mL of purified water and a solution of 16.06 g of ammonium acetate dissolved in 150 mL of purified water at the same time with agitation. Then, to the slurry was further added a solution prepared by dissolving 11.09 g of cupric acetate monohydrate in 170 mL of purified water and the resultant solution was aged at 15 to 20° C. for one hour to yield a green blue slurry.

Then, the resultant slurry was heated in a water bath to be evaporated and dried. The residue was ground with a mortar to cause the size to be 300 µm or less, thereby yielding a dried slurry. The composition of the resultant dried slurry is:

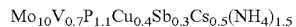

$Mo_{10}V_{0.7}P_{1.1}Cu_{0.4}Sb_{0.3}Cs_{0.5}(NH_4)_{1.5}$

Then, 215.9 g of the resultant dried slurry was uniformly blended with 29.8 g of a strength-improving material (ceramic fiber), and 200 g of a spherical, porous alumina carrier (particle diameter of 3.5 mm, pore ratio of 25.5%) was coated with the resulting mixture leading to a coated molded product using an aqueous 90 wt % ethanol solution as a binder by coating-mold by means of the rolling granulating process. During this process, the loss of powder was rarely observed.

Subsequently, the resultant coated molded product was calcined under a flow of air at 310° C. for five hours, thereby yielding a coated catalyst of the present invention. The particle diameter of the coated catalyst obtained was 4.3 mm (average value).

2) Catalytic Oxidation of Methacrolein

Into a stainless steel reaction tube with an inside diameter of 18.4 mm was introduced 10.3 mL of the resultant coated catalyst, and the oxidation of methacrolein was carried out at a space velocity (SV) of 1200 hr$^{-1}$ and at a reaction bath temperature of 310° C., with a raw material composition in terms of the molar ratio of methacrolein to oxygen to water vapor to nitrogen being 1:2.0:4.0:18.6. First, the reaction results were determined at a reaction bath temperature of 310° C., and then the reaction bath temperature was risen to 350° C. and a reaction was allowed to continue for another 15 hours. Then, the reaction bath temperature was decreased to 310° C. and the reaction results were determined. Table 1 shows the reaction results.

TABLE 1

|  | PT(° C.) | Conversion degree (%) | Selectivity (%) | Yield (%) |
|---|---|---|---|---|
| Initial stage of reaction | 330 | 70.0 | 83.8 | 58.7 |
| After 15 hr at 350°C. | 327 | 83.4 | 83.1 | 69.3 |

\* Pt: Peak or Highest Temperature (the same in Tables below)
\* Conversion degree: conversion degree of methacrolein (the same in Tables below)
\* Selectivity: selectivity of methacrolein (the same in Tables below)
\* Yield: yield of methacrolein (the same in Tables below)

Example 2

1) Preparation of Catalyst

To 2500 mL of purified water were added 350 g of molybdenum trioxide, 17.69 g of vanadium pentaoxide and 32.27 g of 85 wt % orthophosphoric acid, and the solution was heated at reflux at 90 to 100° C. for five hours to yield a reddish-brown, transparent solution.

Subsequently, to the solution was added 17.71 g of antimony trioxide and the resultant solution was further heated at reflux at 90 to 100° C. for two hours to obtain an antimony trioxide-dissolved, highly dark blue solution.

Then, the resulting solution was cooled to from 15 to 20° C. To the solution were gradually added a solution of 23.33 g of cesium acetate dissolved in 170 mL of purified water and a solution of 33.73 g of ammonium acetate dissolved in 170 mL of purified water at the same time with agitation and the resultant solution was aged at 15 to 20° C. for one hour to yield a green blue slurry.

Then, the resultant slurry was heated in a water bath to be evaporated and dried. The residue was ground with a mortar to cause the size to be 300 µm or less, thereby yielding a powder. The composition of the resultant powder is:

$Mo_{10}V_{0.8}P_{1.15}Sb_{0.4}Cs_{0.5}(NH_4)_{1.8}$

Then, to the powder above were added 19.41 g of a powder of cupric acetate monohydrate in which the atomic ratio of the Cu to the Mo is 0.4:10 and 66.1 g of a strength-improving material (ceramic fiber), and the resulting material was mixed uniformly, and then 444.1 g of a spherical, porous alumina carrier (particle diameter of 3.5 mm, pore ratio of 25.5%) was coated with the resulting mixture leading to a coated molded product using an aqueous 90 wt % ethanol solution as a binder by coating-mold by means of the rolling granulating process. The particle diameter of the coated catalyst obtained was 4.3 mm (average value).

The resultant coated molded product was calcined at 380° C. for 10 hours using ethanol (20 g/h) as a reducing agent under a flow of nitrogen (5 L/min) with a box-shaped hot-air circulating calcining furnace to yield a coated catalyst of the present invention. The active components composition of the resulting coated catalyst is:

$Mo_{10}V_{0.8}P_{1.15}Cu_{0.4}Sb_{0.4}Cs_{0.5}(NH_4)_{1.8}$

2) Catalytic Oxidation of Methacrolein

As in Example 1 except using the resultant coated catalyst, oxidation was carried out. The reaction results are indicated in Table 2.

TABLE 2

|  | PT(° C.) | Conversion degree (%) | Selectivity (%) | Yield (%) |
|---|---|---|---|---|
| Initial stage of reaction | 327 | 86.5 | 76.8 | 66.5 |
| After 15 hr at 350° C. | 323 | 85.2 | 86.4 | 73.6 |

Example 3

1) Preparation of Catalyst

To 1400 mL of purified water were added 200 g of molybdenum trioxide, 10.11 g of vanadium pentaoxide and 18.42 g of 85 wt % orthophosphoric acid, and the solution was heated at reflux at 90 to 100° C. for five hours to yield a reddish-brown, transparent solution.

Then, the resulting solution was cooled to from 15 to 20° C. To the solution were gradually added a solution of 13.33 g of cesium acetate dissolved in 100 mL of purified water and a solution of 19.27 g of ammonium acetate dissolved in 100 mL of purified water at the same time with agitation and the resultant solution was aged at 15 to 20° C. for one hour to yield a green blue slurry.

Then, the resultant slurry was heated in a water bath to be evaporated and dried. The residue was ground with a mortar to cause the size to be 300 µm or less, thereby yielding a powder. The composition of the resultant powder is:

$Mo_{10}V_{0.8}P_{1.15}Cs_{0.5}(NH_4)_{1.8}$

Then, to the powder above were added 11.09 g of a powder of cupric acetate monohydrate in which the atomic ratio of the Cu to the Mo is 0.4:10 and 28.9 g of a strength-improving material (ceramic fiber), and the resulting material was mixed uniformly, and then 200 g of a spherical, porous alumina carrier (particle diameter of 3.5 mm, pore ratio of 25.5%) was coated with the resulting mixture leading to a coated molded product using an aqueous 90 wt % ethanol solution as a binder by coating-mold by means of the rolling granulating process. The particle diameter of the coated catalyst obtained was 4.3 mm (average value).

The resultant coated molded product was calcined at 380° C. for 10 hours with ethanol (20 g/h) as a reducing agent under a flow of nitrogen (5 L/min) using a box-shaped hot-air circulating calcining furnace to yield a coated catalyst of the present invention. The active components composition of the resulting coated catalyst is:

$Mo_{10}V_{0.8}P_{1.15}Cu_{0.4}Cs_{0.5}(NH_4)_{1.8}$

2) Catalytic Oxidation of Methacrolein

As in Example 1 except using the resultant coated catalyst, oxidation was carried out. The reaction results are indicated in Table 3.

TABLE 3

|  | PT(° C.) | Conversion degree (%) | Selectivity (%) | Yield (%) |
|---|---|---|---|---|
| Initial stage of reaction | 325 | 83.5 | 80.2 | 66.9 |
| After 15 hr at 350° C. | 323 | 84.9 | 83.4 | 70.3 |

Comparative Example 1

1) Preparation of Catalyst

To 1500 mL of purified water were added 200 g of molybdenum trioxide, 8.84 g of vanadium pentaoxide and 18.42 g of 85 wt % orthophosphoric acid, and the solution was heated at reflux at 90 to 100° C. for five hours to yield a reddish-brown, transparent solution.

Subsequently, to the solution was added 6.07 g of antimony trioxide and the resultant solution was further heated at reflux at 90 to 100° C. for two hours to obtain an antimony trioxide-dissolved, highly dark blue solution.

Then, the resulting solution was cooled to from 15 to 20° C. To the solution were gradually added a solution of 13.54 g of cesium nitrate dissolved in 200 mL of purified water and a solution of a 28% aqueous ammonia solution (26.08 g) diluted in 150 mL of purified water at the same time with agitation and the resultant solution was aged at 15 to 20° C. for one hour to yield a green blue slurry.

Then, the resultant slurry was heated in a water bath to be evaporated and dried. The residue was ground with a mortar to cause the size to be 300 μm or less, thereby yielding a powder. The composition of the resultant powder is:

$Mo_{10}V_{0.7}P_{1.15}Sb_{0.3}Cs_{0.5}(NH_4)_{1.5}$

Then, to the powder above were added 11.09 g of a powder of cupric acetate monohydrate in which the atomic ratio of the Cu to the Mo is 0.4:10 and 34.7 g of a strength-improving material (ceramic fiber), and the resulting material was mixed uniformly, and then 232.6 g of a spherical, porous alumina carrier (particle diameter of 3.5 mm, pore ratio of 25.5%) was coated with the resulting mixture leading to a coated molded product using an aqueous 90 wt % ethanol solution as a binder by coating-mold by means of the rolling granulating process. The particle diameter of the coated molded product obtained was 4.3 mm (average value).

The resultant coated molded product was calcined at 310° C. for five hours under a flow of air to yield a coated catalyst for comparison. The composition of the resulting coated catalyst is:

$Mo_{10}V_{0.7}P_{1.15}Cu_{0.4}Sb_{0.3}Cs_{0.5}(NH_4)_{1.5}$

2) Catalytic Oxidation of Methacrolein

The resultant coated catalyst was subjected to oxidation as in Example 1 with the exception that the reaction bath temperature was 310° C. only. The reaction results are shown in Table 4.

TABLE 4

| PT(° C.) | Conversion degree (%) | Selectivity (%) | Yield (%) |
|---|---|---|---|
| 319 | 33.0 | 74.6 | 24.6 |

Example 4

A coated catalyst of the present invention was obtained as in the case of Example 2 with the exception that the amount of antimony trioxide was changed into 22.14 g, that the amount of ammonium acetate was changed into 26.23 g, and that calcining step conditions were changed into being under a flow of air at 310° C. for five hours. The particle diameter of the resultant coated catalyst was 4.3 mm (average value).

Example 5

A coated catalyst of the present invention was obtained as in the case of Example 2 with the exception that the amount of vanadium pentaoxide was changed into 15.48 g, that the amount of 85 wt % orthophosphoric acid was changed into 31.71 g, that the amount of ammonium acetate was changed into 31.86 g, and that calcining step conditions were changed into being under a flow of air at 310° C. for five hours. The particle diameter of the resultant coated catalyst was 4.3 mm (average value).

Example 6

A coated catalyst of the present invention was obtained as in the case of Example 2 with the exception that a solution of 23.33 g of cesium acetate in 170 mL water was changed into a solution of 20.41 g of cesium hydroxide monohydrate in 175 mL water (the ratio of Cs:Mo being 0.5:10). The particle diameter of the resultant coated catalyst was 4.3 mm (average value).

Example 7

A coated catalyst of the present invention was obtained as in the case of Example 2 with the exception that a solution of 23.33 g cesium acetate in 170 mL water was changed into a solution prepared by adding a solution of 7.30 g of acetic acid in 52.5 mL water to a solution of 20.41 g of cesium hydroxide monohydrate in 123 mL water. The particle diameter of the resultant coated catalyst was 4.3 mm (average value).

Example 8

A coated catalyst of the present invention was obtained as in the case of Example 2 with the exception that the amount of antimony trioxide was changed into 2.21 g. The particle diameter of the resultant coated catalyst was 4.3 mm (average value).

Example 9

A coated catalyst of the present invention was obtained as in the case of Example 3 with the exception that the amount of ammonium acetate was changed into 21.41 g, and that antimony trioxide was not used. The particle diameter of the resultant coated catalyst was 4.3 mm (average value).

Example 10

A coated catalyst of the present invention was obtained as in the case of Example 2 with the exception that the cooling temperature of the antimony trioxide-dissolved, highly dark blue solution was changed into 26 to 30° C. The particle diameter of the resultant coated catalyst was 4.3 mm (average value).

Comparative Example 2

A coated catalyst for comparison was obtained as in the case of Comparative Example 1 with the exception that ammonium acetate was not used, and that the amounts of 85 wt % orthophosphoric acid and antimony trioxide were changed into 20.09 g and 8.09, respectively. The particle diameter of the resultant coated catalyst was 4.3 mm (average value).

Comparative Example 3

A coated catalyst for comparison was obtained as in the case of Example 2 with the exception that cesium acetate and ammonium acetate were not used, and that the amount of cupric acetate monohydrate was changed into 24.26 g. The particle diameter of the resultant coated catalyst was 4.3 mm (average value).

Comparative Example 4

A coated catalyst for comparison was obtained as in the case of Example 2 with the exception that cesium acetate was not used. The particle diameter of the resultant coated catalyst was 4.3 mm (average value).

Comparative Example 5

A coated catalyst for comparison was obtained as in the case of Comparative Example 1 with the exception that the amount of 85 wt % orthophosphoric acid was changed into 19.22 g, and that 13.54 g of cesium nitrate was changed into 7.02 g of potassium acetate. The particle diameter of the resultant coated catalyst was 4.3 mm (average value).

Comparative Example 6

A coated catalyst for comparison was obtained as in the case of Comparative Example 1 with the exception that the amount of 85 wt % orthophosphoric acid was changed into 19.22 g, and that 13.54 g of cesium nitrate was changed into 10.25 g of rubidium acetate. The particle diameter of the resultant coated catalyst was 4.3 mm (average value).

Test Example

The coated catalysts obtained from Examples 4 to 10 and Comparative Examples 2 to 6 were oxidized as in the case of Example 1 at a bath temperature of 350° C. for 15 hours, and subsequently the bath temperature was decreased to 310° C. and the reaction attributes were determined. The results are shown in Table 5 together with the atomic ratio of each catalyst active component of the coated catalysts.

TABLE 5

|  | Catalyst active components composition | | | | | | | PT | Catalyst performance | | |
|---|---|---|---|---|---|---|---|---|---|---|---|
|  | Mo | V | P | Cu | Cs | $NH_4$ | Sb | (° C.) | Conversion degree (%) | Selectivity (%) | Yield (%) |
| Example 4 | 10 | 0.8 | 1.15 | 0.4 | 0.5 | 1.4 | 0.5 | 323 | 85.0 | 83.9 | 71.4 |
| Example 5 | 10 | 0.7 | 1.13 | 0.4 | 0.5 | 1.7 | 0.4 | 317 | 89.0 | 79.7 | 70.9 |
| Example 6 | 10 | 0.8 | 1.15 | 0.4 | 0.5 | 1.8 | 0.4 | 322 | 81.9 | 86.4 | 70.8 |
| Example 7 | 10 | 0.8 | 1.15 | 0.4 | 0.5 | 1.8 | 0.4 | 323 | 83.6 | 85.1 | 71.1 |
| Example 8 | 10 | 0.8 | 1.15 | 0.4 | 0.5 | 1.8 | 0.05 | 321 | 80.6 | 85.6 | 69.0 |
| Example 9 | 10 | 0.8 | 1.15 | 0.4 | 0.5 | 2.0 | — | 322 | 80.2 | 86.3 | 69.2 |
| Example 10 | 10 | 0.8 | 1.15 | 0.4 | 0.5 | 1.8 | 0.4 | 323 | 83.7 | 85.0 | 71.2 |
| Comparative Example 2 | 10 | 0.7 | 1.2 | 0.4 | 0.5 | — | 0.4 | 331 | 88.7 | 70.8 | 62.8 |
| Comparative Example 3 | 10 | 0.8 | 1.15 | 0.5 | — | — | 0.4 | 320 | 60.7 | 79.2 | 48.1 |
| Comparative Example 4 | 10 | 0.8 | 1.15 | 0.4 | — | 1.8 | 0.4 | 311 | 10.1 | 53.0 | 5.3 |
| Comparative Example 5 | 10 | 0.7 | 1.2 | 0.4 | 0.5 (K) | 1.5 | 0.3 | 312 | 11.1 | 65.4 | 7.2 |
| Comparative Example 6 | 10 | 0.7 | 1.2 | 0.4 | 0.5 (Rb) | 1.5 | 0.3 | 314 | 35.6 | 85.5 | 30.5 |

The invention claimed is:

1. A method for preparing a catalyst for producing methacrylic acid by subjecting methacrolein, isobutylaldehyde or isobutyric acid to gas phase catalytic oxidation, the method comprising:

step (A) of blending compounds A-1 to A-3 and, as needed, compound A-4 with water to prepare an aqueous solution or dispersion of the compounds (hereinafter, called a slurry, including both), wherein the compound A-1 is a compound containing Mo, a compound containing V, a compound containing P, and a compound containing Cu, the compound A-2 is cesium acetate or cesium hydroxide, the compound A-3 is ammonium acetate, and the compound A-4 is one or more compounds selected from the group consisting of compounds containing one of Sb, As, Ag, Mg, Zn, Al, B, Ge, Sn, Pb, Ti, Zr, Cr, Re, Bi, W, Fe, Co, Ni, Ce, Th, K and Rb; and step (B) of drying the slurry yielded in step (A) to obtain a dried slurry.

2. The method for preparing the catalyst according to claim 1, wherein the compound A-4 is used as an essential component.

3. A method for preparing a coated catalyst for producing methacrylic acid by subjecting methacrolein, isobutylaldehyde or isobutyric acid to gas phase catalytic oxidation, the method comprising:

step (a) of blending compounds a-1 to a-3 and, as needed, compound a-4 with water to prepare an aqueous solution or dispersion of the compounds (hereinafter, called a slurry, including both), wherein the compound a-1 is a compound containing Mo, a compound containing V, a compound containing P, and a compound containing Cu, the compound a-2 is cesium acetate or cesium hydroxide, the compound a-3 is ammonium acetate, and the compound a-4 is one or more compounds selected from the group consisting of compounds containing one of Sb, As, Ag, Mg, Zn, Al, B, Ge, Sn, Pb, Ti, Zr, Cr, Re, Bi, W, Fe, Co, Ni, Ce, Th, K and Rb;

step (b) of drying the slurry yielded in step (a) to obtain a dried slurry;

step (c) of coating a carrier with the dried slurry obtained in step (b) using a binder to obtain a coated molded product; and step (d) of calcining the coated molded product obtained in step (c).

4. A method for preparing a coated catalyst for producing methacrylic acid by subjecting methacrolein, isobutylaldehyde or isobutyric acid to gas phase catalytic oxidation, the method comprising:

step (a) of blending compounds a-1 to a-3 and, as needed, compound a-4 with water to prepare a slurry of the compounds, wherein the compound a-1 is a compound containing Mo, a compound containing V, a compound containing P, and a compound containing Cu, the compound a-2 is cesium acetate or cesium hydroxide, the compound a-3 is ammonium acetate, and the compound a-4 is one or more compounds selected from the group consisting of compounds containing one of Sb, As, Ag, Mg, Zn, Al, B, Ge, Sn, Pb, Ti, Zr, Cr, Re, Bi, W, Fe, Co, Ni, Ce, Th, K and Rb;

step (b) of drying the slurry yielded in step (a) to obtain a dried slurry;

step (b') of blending the dried slurry obtained in step (b) with a solid compound containing copper to obtain powders;

step (c) of coating a carrier with the powders obtained in step (b') using a binder to obtain a coated molded product; and step (d) of calcining the coated molded product obtained in step (c).

5. The method for preparing the coated catalyst according to claim 3 or 4, wherein the compound a-4 is used as an essential component.

6. The method for preparing the coated catalyst according to claim 3 or 4, wherein at least one species selected from the group consisting of water and organic compounds having a boiling point of 150° C. or lower at one atmospheric pressure is used as a binder.

7. The method for preparing the coated catalyst according to claim 6, wherein the binder is ethanol.

8. The method for preparing the coated catalyst according to claim 6, wherein the binder has a weight ratio of ethanol to water being from 10:0 to 5:5.

9. The method for preparing the coated catalyst according to claim 3 or 4, wherein the coated molded product is calcined in the presence of a reducing agent in step (d).

10. The method for preparing the coated catalyst according to claim 9, wherein the reducing agent is ethanol.

* * * * *